United States Patent [19]

Steiner et al.

[11] 4,399,139
[45] Aug. 16, 1983

[54] 5,6-DIHYDRO-11-ALKYLENE-MORPHAN-THRIDIN-6-ONES, THEIR PHARMACEUTICAL COMPOSITIONS AND METHOD OF USE

[75] Inventors: Gerd Steiner, Kirchheim; Ludwig Friedrich, Bruehl; Dieter Lenke, Ludwigshafen, all of Fed. Rep. of Germany

[73] Assignee: BASF Aktiengesellschaft, Fed. Rep. of Germany

[21] Appl. No.: 359,936

[22] Filed: Mar. 19, 1982

[30] Foreign Application Priority Data

Apr. 1, 1981 [DE] Fed. Rep. of Germany ....... 3113094

[51] Int. Cl.³ ..................... A61K 31/55; C07D 403/06
[52] U.S. Cl. .................................... 424/250; 424/244; 260/239.3 T
[58] Field of Search ................ 260/239.3 T; 424/244, 424/250

[56] References Cited

U.S. PATENT DOCUMENTS 4,336,192 8/1982 Steiner et al. ................ 260/239.3 T

FOREIGN PATENT DOCUMENTS 1795183 7/1972 Fed. Rep. of Germany ... 260/239.3 T
2724501 5/1977 Fed. Rep. of Germany ... 260/239.3 T
4210648 7/1980 Fed. Rep. of Germany ... 260/239.3 T
1144829 3/1969 United Kingdom ......... 260/239.3 T

OTHER PUBLICATIONS

Arzneim-Forsch. 27 (1977), pp. 356–359.

Primary Examiner—Robert T. Bond
Attorney, Agent, or Firm—Keil & Witherspoon

[57] ABSTRACT

Novel 5,6-dihydro-11-alkylene-morphanthridin-6-ones of the formula

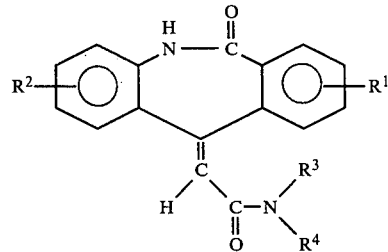

where $R^1$, $R^2$, $R^3$ and $R^4$ have the meanings given in the description, their preparation and their use.

The novel compounds are particularly useful in the treatment of gastric and duodenal ulcers.

6 Claims, No Drawings

5,6-DIHYDRO-11-ALKYLENE-MORPHANTHRI-DIN-6-ONES, THEIR PHARMACEUTICAL COMPOSITIONS AND METHOD OF USE

The present invention relates to 5,6-dihydro-11-alkylene-morphanthridin-6-ones, their preparation, therapeutic agents containing these compounds, and their use as drugs.

It is known (Arzneim.-Forsch. 27 (1977), 356; German Laid-Open Applications DOS Nos. 2,724,501 and 2,724,478) that tricyclic ring systems of the 5,11-dihydro-6H-pyrido[2,3-b][1,4]benzodiazepin-6-one type possess valuable properties which can be utilized in the treatment of gastric and duodenal ulcers.

We have found that 5,6-dihydro-11-alkylene-morphanthridin-6-ones of the formula I

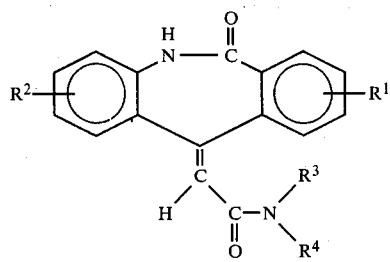

where $R^1$ and $R^2$ are hydrogen, halogen, alkyl of 1 to 3 carbon atoms or trifluoromethyl and $R^3$ is alkyl of 1 to 5 carbon atoms, cycloalkyl or cycloalkyl-methyl, in both of which the cycloalkyl ring is of 3 to 6 carbon atoms and may contain a nitrogen atom which is unsubstituted or substituted by alkyl of 1 to 3 carbon atoms or is in the form of the N-oxide, hydroxyalkyl of 2 to 5 carbon atoms, alkoxy of 2 to 5 carbon atoms, aminoalkyl of 2 to 7 carbon atoms, the amine nitrogen being unsubstituted or substituted by alkyl of 1 to 5 carbon atoms or being a member of a 5-membered to 7-membered saturated ring which may contain a nitrogen or oxygen atom as an additional hetero-atom, the nitrogen, if present, being substituted by alkyl of 1 to 3 carbon atoms, hydroxyalkyl of 2 or 3 carbon atoms or phenyl, which itself is unsubstituted or substituted by fluorine, chlorine, methoxy or methyl, $R^4$ has one of the meanings given for $R^3$ or is hydrogen, or $R^3$ and $R^4$ together with the nitrogen atom by which they are linked form a 5-membered to 7-membered saturated ring which may be substituted by one or more alkyl radicals of 1 to 3 carbon atoms or may additionally contain a nitrogen or oxygen atom, the additional nitrogen, if present, being unsubstituted or substituted by alkyl of 1 to 3 carbon atoms, cycloalkyl of 5 to 6 carbon atoms in the ring, hydroxyalkyl of 2 or 3 carbon atoms, alkoxyalkyl of 1 to 3 carbon atoms in the alkyl and alkoxy radical or phenyl, which is itself unsubstituted or substituted by fluorine, chlorine, methoxy or methyl, or being in the form of the N-oxide, and/or their physiologically tolerated addition salts with acids possess valuable pharmacological properties.

The novel compounds of the formula I can be in the form of the cis- and trans-isomers Ia and Ib:

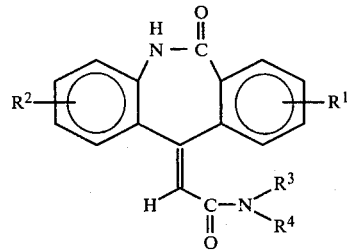

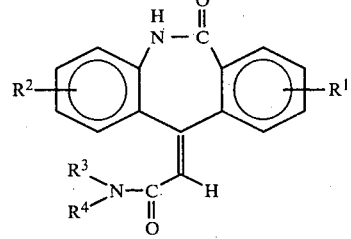

$R^1$ and $R^2$ are preferably hydrogen, chlorine or methyl.

Specific examples of radicals $R^3$ and $R^4$, provided one of them is hydrogen, are 2-aminoethyl, 2-dimethylaminoethyl, 3-dimethylaminopropyl, 2-diethylaminoethyl, 3-diethylaminopropyl, 2-methylaminoethyl, 2-hydroxyethyl, 2-piperidin-1-yl-ethyl, 2-pyrrolidin-1-yl-ethyl, 3-piperidin-1-yl-propyl, 2-morpholin-1-yl-ethyl, 3-morpholin-1-yl-propyl, 2-piperazin-1-yl-ethyl, 1-methoxyprop-1-yl, 3-(4-methylpiperazin-1-yl)-propyl, 1-ethylpyrrolidin-2-yl-methyl, 3-(4-methylpiperazin-1-yl)-propyl and N-methylpiperidin-4-yl.

Particularly suitable amine radicals $-NR^3R^4$, if $R^3$ and $R^4$ are not hydrogen, include bis-(2-hydroxyethyl)-amino, N-methyl-2-(N',N'-dimethylamino)-ethylamino, N-methyl-(N'-methylpiperidin-4-yl)-amino and dimethylamino-bis-n-butylamino.

Examples of amine radicals $-NR^3R^4$, where $R^3$ and $R^4$ together are a 5-membered to 7-membered saturated ring, which may contain a nitrogen atom or oxygen atom as a further hetero-atom, include piperazinyl, homopiperazinyl, piperidinyl, pyrrolidinyl, hexahydroazepinyl and morpholinyl. Preferred radicals are piperazin-1-yl, 4-methyl-piperazin-1-yl, 4-methyl-4-oxy-piperazin-1-yl, 4-ethyl-piperazin-1-yl, 4-(2-hydroxyethyl)-piperazin-1-yl, N-methyl-homopiperazin-1-yl and 4-phenyl-piperazin-1-yl; 4-methyl-piperazin-1-yl is particularly preferred.

Examples of particularly active compounds are the following: cis,trans-11-(4-methyl-piperazin-1-yl)-carboxamidomethylene-5,6-dihydro-morphanthridin-6-one, cis-11-(4-methyl-piperazin-1-yl)-carboxamidomethylene-5,6-dihydro-morphanthridin-6-one, cis,trans-11-(4-ethyl-piperazin-1-yl)-carboxamidomethylene-5,6-dihydro-morphanthridin-6-one, cis,trans-11-(4-methyl-4-oxy-piperazin-1-yl)-carboxamidomethylene-5,6-dihydro-morphanthridin-6-one, cis,trans-2-chloro-11-(4-methyl-piperazin-1-yl)-carboxamidomethylene-5,6-dihydro-morphanthridin-6-one and cis,trans-2-methyl-11-(4-methyl-piperazin-1-yl)-carboxamidomethylene-5,6-dihydro-morphanthridin-6-one.

Amongst these compounds, the cis-isomers are preferred.

The novel compounds of the formula I are obtained when (a) a compound of the formula II

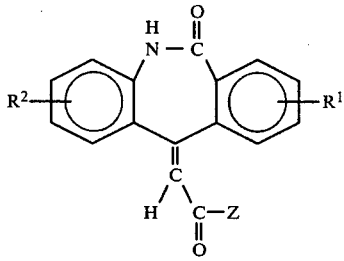

where $R^1$ and $R^2$ have the stated meanings and Z is a nucleofugic leaving group, is reacted with an amine $HNR^3R^4$, where $R^3$ and $R^4$ have the stated meanings, or (b) a 5,6-dihydro-morphanthridine-6,11-dione of the formula V

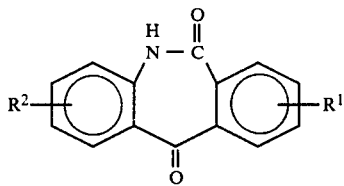

where $R^1$ and $R^2$ have the stated meanings, is reacted with a phosphonate of the formula VI

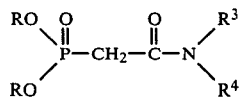

where R is alkyl of 1 to 3 carbon atoms and $R^3$ and $R^4$ have the stated meanings, under the conditions of a Wittig reaction, in an inert solvent in the presence of one mole equivalent of a base, at from 20° to 80° C., and, if desired, the resulting compound is separated into the pure cis-isomer and trans-isomer and/or is converted to an addition salt with a physiologically tolerated acid.

Suitable nucleofugic leaving groups Z include halogen atoms, especially chlorine.

Reaction (a) is advantageously carried out in the presence of one mole equivalent of a tertiary amine, eg. triethylamine, in an inert solvent, such as a cyclic saturated ether, especially tetrahydrofuran or dioxane, or a polar aprotic solvent, preferably dimethylformamide, at from 0° to 150° C., preferably from 20° to 80° C., and is in general complete within from 3 to 10 hours.

If desired, the reaction may also be carried out in the presence of an excess of the amine $HNR^3R^4$ employed, which at the same time serves as the solvent and, where appropriate, as an acid acceptor.

The reaction (b) is preferably carried out in dimethylformamide as the solvent. Particularly suitable bases are a sodium alcoholate, sodium hydride, sodium amide or an organo-metallic compound, eg. n-butyl-lithium.

A compound of the formula I is converted to the N-oxide in a conventional manner, advantageously with aqueous (30% strength by weight) hydrogen peroxide in ethanol solution. Conversion to the addition salt with a physiologically tolerated acid is also carried out in a conventional manner.

The compounds of the formula I are as a rule obtained as crystals and can be purified by recrystallization from the conventional organic solvents, preferably from a lower alcohol, eg. ethanol, or a lower ester, preferably ethyl acetate, or by column chromatography.

The phosphonates of the formula VI are either known or can be prepared by an Arbusov reaction from the corresponding haloalkanoic acid amide and trialkyl phosphite.

The cis-trans isomer mixture can be separated by fractional crystallization or by column chromatography. Fractional crystallization can be effected in a lower ester, preferably ethyl acetate, or a lower monohydric alcohol, eg. methanol or ethanol. Separation by column chromatography is particularly successful if carried out over silica gel, using methylene chloride, or a mixture of methylene chloride and methanol in a volume ratio of from 99:1 to 85:15.

The structure of the individual isomers is allocated on the basis of, for example, X-ray structural analysis.

If desired, the novel compounds obtained are converted to addition salts with a physiologically tolerated acid. Examples of conventional physiologically tolerated acids are, amongst inorganic acids, hydrochloric acid, hydrobromic acid, phosphoric acid and sulfuric acid and, amongst organic acids, oxalic acid, maleic acid, fumaric acid, lactic acid, tartaric acid, malic acid, citric acid, salicyclic acid, adipic acid and benzoic acid; further examples may be found in J. Pharmaceut. Sci., 66 (1977), 1–5.

The addition salts with acids are as a rule obtained in a conventional manner by mixing the free base or a solution thereof with the appropriate acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. Mixtures of the said solvents may also be used, to ensure better crystallization.

A starting compound of the formula II is obtained by converting a cis,trans-11-carboxymethylene-5,6-dihydromorphanthridin-6-one of the formula III

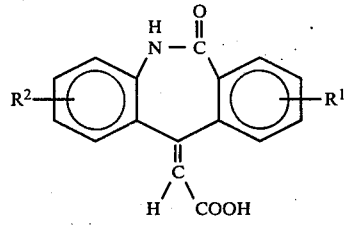

where $R^1$ and $R^2$ have the stated meanings, to the carboxylic acid halide in the conventional manner by means of excess thionyl chloride at room temperature.

A compound of the formula III is obtained by hydrolyzing the corresponding ester (German Laid-Open Application DOS. No. 2,918,832) with alcoholic alkali metal hydroxide solution at from 40° to 90° C.

The novel compounds and their physiologically tolerated addition salts with acids are drugs which are valuable in the treatment of disorders associated with pathologically increased gastric secretion, for example gastric ulcers and duodenal ulcers.

The inhibition of gastric acid secretion manifests itself in a rise in the pH of the gastric mucosa. It is tested on groups of 5 conscious female Sprague-Dawley rats (160–180 g). The animals are kept without food (but with water ad libitum) for 48 hours and are then pretreated with varying doses of the test substances, administered subcutaneously. After 1 hour, they are narcotized with Na hexobarbital (46.4 mg/kg, given intravenously). A pH electrode (Philips Special Electrode, type CJP) is then introduced into the stomach and the pH at the surface of the gastric mucosa is measured (pH in the untreated animals is $1.40\pm0.02$; $N=200$). The ED 0.75, ie. the dose which causes an increase in pH averaging 0.75, compared to the pH in the untreated control animals, is determined from the linear regression between logarithm of administered dose and increase in pH.

To examine the anti-ulcerogenic effect, groups of 10 female Sprague-Dawley rats (weighing 160–180 g) are given 1 mg/kg of reserpine intraperitoneally, and are then left for 18 hours without food (but with water ad libitum). After this time, the animals are given 21.5 mg/kg of indomethacin intraperitoneally and the test substance orally; they are then kept for 6 hours at 8° C., after which they are killed. The stomachs are removed and the surface area of ulcerous lesions is determined. The ED 50%, ie. the dose which reduces the ulcerated surface area by 50%, is determined from the linear regression between logarithm of administered dose and reduction in the surface area of the ulcerations relative to that in the control animals.

To determine anti-cholinergic side-effects (mydriasis, inhibition of salivation), groups of from 5 to 10 female Sprague-Dawley rats (160–200 g) are given the test substance subcutaneously. After 1 hour, the pupil diameter is measured. The animals are then given 0.6 mg/kg of carbachol intraperitoneally. After 5 minutes, the saliva secreted as a result of stimulation by carbachol is blotted up with 4 cm wide strips of universal indicator paper (from Merck). The surface area of the paper colored blue by the alkaline saliva serves as a measure of the salivary secretion. The test substance is taken to inhibit salivary secretion if the blue area of the paper is more than 50% smaller than in the case of the controls. Evaluation of the linear relationships between the logarithms of the dose and the frequency of inhibition of salivation is carried out alternatively by Probit analysis. The ED 50 is taken to be the dose at which the relative frequency of inhibition of salivation is 50%.

If there is a mydriatic effect, there is a linear regression between the logarithm of the dose and the increase in pupil diameter in mm, from which the ED 2 mm, ie. the dose which increases the pupil diameter by 2 mm, is calculated.

The reference substance used is pirenzepine (5,11-dihydro-11-[(4-methyl-piperazin-1-yl)-acethyl]-6H-pyrido-[2,3,b][1,4]-benzodiazepin-6-one, cf. German Pat. No. 1,795,183).

The novel compounds inhibit the secretion of acid in the stomach, as evidenced by a dose-dependent increase in pH at the surface of the gastric mucosa (Table 1). They also inhibit the genesis of gastric ulcers (Table 2). In both tests, the substances prove more effective than the known drug pirenzepine (German Pat. No. 1,795,183). Moreover their action is more specific than that of pirenzepine, as revealed by a substantially greater gap between the secretion-inhibiting doses and the doses which produce undesirable anti-cholinergic side-effects such as mydriasis or inhibition of salivation (Table 1).

TABLE 1

Inhibition of gastric secretion, and anti-cholinergic action, in the rat

| Test model | | Example 1 cis/trans | Example 1 cis | Pirenzepine |
|---|---|---|---|---|
| Inhibition of gastric acid secretion | ED 0.75 R.E. | 0.055 >1.6 | 0.032 2.7 | 0.086 1.0 |
| Mydriatic action | ED 2 mm ED 2 mm ED 0.75 | >215 >3900 | 198 6200 | 1.6 19 |
| Salivation-inhibiting action | ED 50 ED 50/ ED 0.75 | 99 1800 | 50 1600 | 2.0 23 |

Administered subcutaneously; R.E. = relative effectiveness
Effective doses in mg/kg

TABLE 2

Anti-ulcerogenic effect in the rat

| Example | ED 50% mg/kg | R.E. |
|---|---|---|
| 1, cis/trans | 2.1 | 3.1 |
| 1, cis | 1.7 | 3.8 |
| Pirenzepine | 6.5 | 1.0 |

Administered orally; R.E. = relative effectiveness

Accordingly, the present invention also relates to drugs which contain a compound of the formula I or a physiologically tolerated acid addition salt thereof, and to the use of the novel compounds in the treatment of disorders which are accompanied by pathologically increased gastric secretion.

The novel compounds may be employed in the conventional solid or liquid pharmaceutical forms, such as tablets, capsules, powders, granules, dragees or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. H. Sucker et al.: Pharmazeutische Technologie, Thieme-Verlag, Stuttgart). The formulations thus obtained normally contain from 0.001 to 99% by weight of the active compound.

The preferred formulations are those suitable for oral administration. Examples of these are tablets, film tablets, dragees, capsules, pills, powders, solutions, suspensions and depot forms. Parenteral formulations, such as infusion solutions, may also be used. Suppositories are a further example of suitable formulations.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn, starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Correspondingly, dragees can be prepared by coating cores, prepared similarly to the tablets, with agents conventionally used in dragee coatings, for example collidone or shellac, gum arabic, talc, titanium dioxide or sugar. The dragee coating can also consist of a plurality of layers, and the auxiliaries mentioned above in connection with tablets may be used therein.

Solutions or suspensions containing the novel active compounds may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The dosage of the compounds according to the invention depends on the age, condition and weight of the patient and on the route of administration. As a rule, the daily dose of active compound is from 5 to 100, preferably from 10 to 80, mg.

The Examples which follow illustrate the invention. The melting points of the cis,trans-isomer mixtures can vary depending on the relative amounts of the two isomers.

EXAMPLE 1 cis- and trans-11-(4-Methylpiperazin-1-yl)-carboxamidomethylene-5,6-dihydromorphanthridin-6-one A. Preparation of the starting material 200 ml of 10% strength sodium hydroxide solution were added to 30.0 g (108 millimoles) of 11-carbomethoxymethylene-5,6-dihydromorphanthridin-6-one in 150 ml of ethanol and the reaction mixture was stirred for 2 hours under reflux. When it had cooled, the mixture was filtered and concentrated, under reduced pressure from a waterpump, to about half its volume. It was then acidified with concentrated hydrochloric acid whilst being cooled with ice, and the crystals which precipitated out were filtered off and washed thoroughly with water. 27 g (94%) of cis,trans-11-carboxymethylene-5,6-dihydromorphanthridin-6-one, of melting point 258°–260° C., were isolated.

200 ml of thionyl chloride were added to 31.0 g (124 millimoles) of the compound thus obtained, and the mixture was stirred at room temperature. Dissolution occurred within 1 hour. After the mixture had been stirred for a further hour, the thionyl chloride was stripped off under reduced pressure from an oilpump, the residue was taken up in a small amount of toluene and the solvent was stripped off again completely. The cis,trans-11-chlorocarbonylmethylene-5,6-dihydromorphanthridin-6-one which remained (99% yield) was sufficiently pure for further conversion.

B. Preparation of the end product 12.9 g (129 millimoles) of N-methylpiperazine and 12.5 g (124 millimoles) of triethyl amine were added, a little at a time, with thorough stirring, to 35.1 g (124 millimoles) of 11-chlorocarbonylmethylene-5,6-dihydromorphanthridin-6-one (cis,trans-isomer mixture) in 140 ml of dimethylformamide, and the resulting mixture was stirred for 2 hours under a nitrogen atmosphere at room temperature. After the solvent had been completely distilled off under reduced pressure, the residue was partitioned between methylene chloride and water, the aqueous phase was rendered slightly alkaline with dilute sodium hydroxide solution and extracted twice more with methylene chloride, and the combined organic phases were thoroughly washed with water. On drying and concentrating the organic phase, 36 g of crude product were obtained.

To prepare the pure cis,trans-isomer mixture, the crude product was purified by column chromatography (silica gel, 95/5 methylene chloride/methanol mixture). 34.0 g (75%) of cis,trans-11-(4-methyl-piperazin-1-yl)-carboxamidomethylene-5,6-dihydromorphanthridin-6-one×H$_2$O, melting point 125°–128° C., were isolated.

To separate the cis and trans isomers, 16.0 g of the isomer mixture were digested in 200 ml of boiling ethyl acetate and the insoluble constituents were filtered off hot. 7.0 g of a colorless solid were obtained. According to a thin layer chromatogram (silica gel, mobile phase: an 85/15 toluene/methanol mixture), the material consisted principally of the non-polar cis-isomer. It was recrystallized from ethyl acetate; melting point 229°–231° C.

The filtrate was concentrated and the residue was taken up in just sufficient boiling ethyl acetate to dissolve all the material. The first fraction which crystallized out in the cold frequently consisted of the isomer mixture. Thereafter, however, about 5 g of the highly enriched polar trans-isomer crystallized out from the residual mother liquor.

A further recrystallization from ethyl acetate gave the pure trans-isomer in the form of colorless crystals, of melting point 219°221° C.

Both isomers contained ¼ mole of water of crystallization. The structures were allocated to the two geometrical isomers by means of X-ray structural analysis.

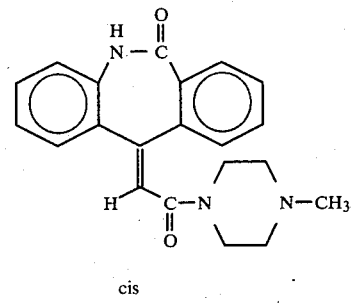

cis

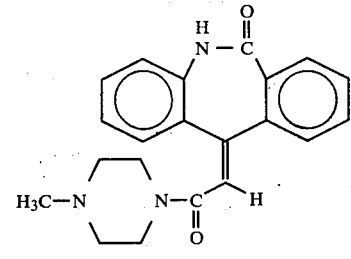

trans

The following were prepared by a method similar to that of Example 1:

2. cis,trans-11-(4-Ethylpiperazin-1-yl)-carboxamidomethylene-5,6-dihydromorphanthridin-6-one×0.5 H$_2$O. Melting point: 112°–115° C.

3. cis,trans-2-Methyl-11-(4-methylpiperazin-1-yl)-carboxamidomethylene-5,6-dihydromorphanthridin-6-one×0.5 H$_2$O. Melting point: 115°117° C.

4. cis,trans-2-Methyl-11-(4-ethylpiperazin-1-yl)-carboxamidomethylene-5,6-dihydromorphanthridin-6-one×0.5 H₂O. Melting point: 116°–117° C.

5. cis,trans-3-Methyl-11-(4-methylpiperazin-1-yl)-carboxamidomethylene-5,6-dihydromorphanthridin-6-one×0.5 H₂O×0.5 HCl. Melting point 117°–118° C.

6. cis,trans-3-Methyl-11-(4-ethylpiperazin-1-yl)-carboxamidomethylene-5,6-dihydromorphanthridin-6-one×H₂O. Melting point: 216°–220° C.

7. cis,trans-2-Chloro-11-(4-methylpiperazin-1-yl)-carboxamidomethylene-5,6-dihydromorphanthridin-6-one×0.5 H₂O. Melting point 230°–232° C.

8. cis,trans-2-Chloro-11-(4-ethylpiperazin-1-yl)-carboxamidomethylene-5,6-dihydromorphanthridin-6-one. Melting point 230°–233° C.

9. cis,trans-11-(N'-methylhomopiperazin-1-yl)-carboxamidomethylene-5,6-dihydromorphanthridin-6-one×1.5 H₂O. Melting point: 126°–129° C.

10. cis,trans-11-(4-β-Hydroxyethylpiperazin-1-yl)-carboxamidomethylene-5,6-dihydromorphanthridin-6-one×H₂O. Melting point: 130°–135° C.

11. cis,trans-11-Piperidin-1-yl-carboxamidomethylene-5,6-dihydromorphanthridin-6-one×0.25 H₂O. Melting point: 188°–190° C.

12. cis,trans-11-(4-Methylpiperidin-1-yl)-carboxamidomethylene-5,6-dihydromorphanthridin-6-one×0.5 H₂O. Melting point 195°–198° C.

13. cis,trans-11-(β-Hydroxyethylamino)-carboxamidomethylene-5,6-dihydromorphanthridin-6-one×2 H₂O. Melting point: 108°–111° C.

14. cis,trans-11-(bis-β-Hydroxyethylamino)-carboxamidomethylene-5,6-dihydromorphanthridin-6-one. Melting point: 105°–110° C.

15. cis,trans-11-(4-Phenylpiperazin-1-yl)-carboxamidomethylene-5,6-dihydromorphanthridin-6-one. Melting point: 229°–231° C.

16. cis,trans-11-(2-Morpholin-1-yl-ethylamino)-carboxamidomethylene-5,6-dihydromorphanthridin-6one×H₂O. Melting point: 125°–128° C.

17. cis,trans-11-(2-Dimethylaminoethylamino)-carboxamidomethylene-5,6-dihydromorphanthridin-6-one×H₂O. Melting point: 123°–125° C.

18. cis,trans-11-(3-Dimethylaminopropylamino)-carboxamidomethylene-5,6-dihydromorphanthridin-6-one×0.5 HCl×0.5 H₂O. Melting point: 128°–130° C.

19. cis,trans-11-(2-Diethylaminoethylamino)-carboxamidomethylene-5,6-dihydromorphanthridin-6-one×0.5 H₂O. Melting point: 108°–110° C.

20. cis,trans-11-(3-Diethylaminopropylamino)-carboxamidomethylene-5,6-dihydromorphanthridin-6-one×H₂O. Melting point: 107°–109° C.

21. cis,trans-11-(2-Methylaminoethylamino)-carboxamidomethylene-5,6-dihydromorphanthridin-6-one×0.5 HCl×0.5 H₂O. Melting point 112°–115° C.

22. cis,trans-11-(2-Piperidin-1-yl-ethylamino)-carboxamidomethylene-5,6-dihydromorphanthridin-6-one×H₂O. Melting point: 123°–125° C.

23. cis,trans-11-(3-Piperidin-1-yl-propylamino)-carboxamidomethylene-5,6-dihydromorphanthridin-6-one×0.5 HCl. Melting point: 121°–123° C.

24. cis,trans-11-[2-(4-Phenyl-piperazin-1-yl)-ethylamino]-carboxamidomethylene-5,6-dihydromorphanthridin-6-one×H₂O. Melting point: 113°–115° C.

25. cis,trans-11-[3-(4-(0-Methoxyphenyl)-piperazin-1-yl)-propylamino]-carboxamidomethylene-5,6-dihydromorphanthridin-6-one×H₂O. Melting point: 118°–120° C.

26. cis,trans-11-Pyrrolidin-1-yl-carboxamidomethylene-5,6-dihydromorphanthridin-6-one×0.5 H₂O. Melting point: 211°–213° C.

27. cis,trans-11-(2-Pyrrolidin-1-yl-ethylamino)-carboxamidomethylene-5,6-dihydromorphanthridin-6-one×H₂O×0.5 HCl. Melting point: 130°–133° C.

28. cis,trans-11-(bis-n-Butylamino)-carboxamidomethylene-5,6-dihydromorphanthridin-6-one×0.25 H₂O. Melting point: 152°–154° C.

29. cis,trans-11-(4-Benzyl-piperazin-1-yl)-carboxamidomethylene-5,6-dihydromorphanthridin-6-one×0.25 HCl. Melting point: 111°–113° C.

30. cis,trans-11-(2,4-Dimethyl-piperazin-1-yl)-carboxamidomethylene-5,6-dihydromorphanthridin-6-one×0.5 HCl. Melting point: 117°–120° C.

31. cis,trans-11-(2,4,6-Trimethyl-piperazin-1-yl)-carboxamidomethylene-5,6-dihydromorphanthridin-6-one×0.75 HCl. Melting point 130°–133° C.

32. cis,trans-11-(2,6-Dimethyl-4-cyclohexyl-piperazin-1-yl)-carboxamidomethylene-5,6-dihydromorphanthridin-6-one×0.25 HCl. Melting point 121°–123° C.

33. cis,trans-11-[2,6-Dimethyl-4-(o-methyl-phenyl)-piperazin-1-yl]-carboxamidomethylene-5,6-dihydromorphanthridin-6-one×0.5 HCl. Melting point 142°–145° C.

34. cis,trans-11-[2,6-Dimethyl-4-(o-methoxy-phenyl)-piperazin-1-yl]-carboxamidomethylene-5,6-dihydromorphanthridin-6-one×0.5 HCl. Melting point: 130°–132° C.

35. cis,trans-11-[2,6-Dimethyl-4-(p-methyl-phenyl)-piperazin-1-yl]-carboxamidomethylene-5,6-dihydromorphanthridin-6-one×0.75 HCl. Melting point: 138°–141° C.

36. cis,trans-11-[3-(4-Methyl-piperazin-1-yl)-but-2-yl-amino]-carboxamidomethylene-5,6-dihydro-morphanthridin-6-one×HCl. Melting point: 138°–140° C.

37. cis,trans-11-[1-(4-Methyl-piperazin-1-yl)-but-2-yl-amino]-carboxamidomethylene-5,6-dihydro-morphanthridin-6-one×H₂O×0.5 HCl. Melting point: 132°–134° C.

38. cis,trans-11-(1-Piperidin-1-yl-prop-2-yl-amino)-carboxamidomethylene-5,6-dihydro-morphanthridin-6-one×0.5 H₂O×0.25 HCl. Melting point: 125°–128° C.

39. cis,trans-11-Hexahydro-azepin-1-yl-carboxamidomethylene-5,6-dihydro-morphanthridin-6-one×0.5 H₂O. Melting point: 115°–117° C.

40. cis,trans-11-(1-Hexahydro-azepin-1-yl-prop-2-yl-amino)-carboxamidomethylene-5,6-dihydro-morphanthridin-6-one×H₂O. Melting point: 120°–123° C.

41. cis,trans-11-(1-Methoxy-prop-2-yl-amino)-carboxamidomethylene-5,6-dihydro-morphanthridin-6-one×0.5 H₂O. Melting point: 87°–89° C.

42. cis,trans-11-(3,5-cis-Dimethyl-morpholin-1-yl)-carboxamidomethylene-5,6-dihydro-morphanthridin-6-one×0.5 H₂O×0.25 HCl. Melting point: 111°–114° C.

43. cis,trans-11-(1-Ethyl-pyrrolidin-2-yl-methylamino)-carboxamidomethylene-5,6-dihydro-morphanthridin-6-one×0.5 HCl. Melting point: 121°–123° C.

44. cis,trans-11-(1-Methyl-piperidin-4-yl-amino)-carboxamidomethylene-5,6-dihydro-morphanthridin-6-one×HCl. Melting point: 156°–159° C.

45. cis,trans-11-(1-Methyl-piperidin-4-yl-N-methylamino)-carboxamidomethylene-5,6-dihydro-morphanthridin-6-one×HCl. Melting point: 128°–130° C.

46. cis,trans-11-(3-Morpholin-1-yl-propylamino)-carboxamidomethylene-5,6-dihydro-morphanthridin-6-one×0.5 H₂O. Melting point: 115°–117° C.

47. cis,trans-11-[3-(4-Methyl-piperazin-1-yl)-propylamino]-carboxamidomethylene-5,6-dihydro-morphanthridin-6-one×H₂O×0.5 HCl. Melting point: 127°–129° C.

48. cis,trans-11-[4-(3-Hydroxy-propyl)-piperazin-1-yl]-carboxamidomethylene-5,6-dihydro-morphanthridin-6-one×0.75 HCl. Melting point: 130°–133° C.

EXAMPLE 49 cis,trans-11-Piperazin-1-yl-carboxamidomethylene-5,6-dihydro-morphanthridin-6-one×2 H₂O 7.0 g (25 millimoles) of 11chlorocarbonylmethylene-5,6-dihydro-morphanthridin-6-one (cis, trans-isomer mixture) in 50 ml of dimethylformamide were added dropwise to a well-stirred solution of 7.8 g (91 millimoles) of piperazine in 50 ml of dimethylformamide, and stirring was continued for 3 hours at room temperature, under a nitrogen atmosphere. The solvent was then distilled off completely under reduced pressure from an oilpump, the residue was partitioned between methylene chloride and water, the aqueous phase was rendered slightly alkaline with dilute sodium hydroxide solution and was extracted twice more with methylene chloride, and the combined organic phases were washed thoroughly with water. On drying and concentrating the organic phase, the crude product was obtained.

To prepare the pure cis,trans-isomer mixture, the crude product was purified by column chromatography (silica gel, mobile phase: a 95/5 methylene chloride/methanol mixture). 31% yield of colorless crystals, melting point 150°–152° C. (with decomposition), were obtained.

Using a method similar to that described in Example 49, the following end products were prepared from the corresponding bifunctional amines:

50. cis,trans-11-(3,5-Dimethyl-piperazin-1-yl)-carboxamidomethylene-5,6-dihydro-morphanthridin-6-one×0.5 HCl. Melting point: 133°–135° C.

51. cis,trans-11-(2-Piperazin-1-yl-ethylamino)-carboxamidomethylene-5,6-dihydro-morphanthridin-6-one×0.5 H₂O×0.5 HCl. Melting point: 110°–112° C.

EXAMPLE 52 cis,trans-11-Dimethylamino-carboxamidomethylene-5,6-dihydro-morphanthridin-6-one×0.5 HCl 3.4 g (75 millimoles) of dimethylamine were passed into 7.0 g (25 millimoles) of 11-chlorocarbonylmethylene-5,6-dihydro-morphanthridin-6-one (cis,trans-isomer mixture) in 40 ml of dimethylformamide, with thorough stirring, and the batch was then stirred for 2 hours at room temperature. The solvent was distilled off completely under reduced pressure, the residue was partitioned between methylene chloride and water, the aqueous phase was rendered slightly alkaline with dilute sodium hydroxide solution and extracted twice more with methylene chloride, and the combined organic phases were thoroughly washed with water. On drying and concentrating the organic phase, the crude product was obtained.

To prepare the pure cis,trans-isomer mixture, the crude product was purified by column chromatography (silica gel, mobile phase: a 95/5 methylene chloride/methanol mixture). 69% of colorless crystals, melting point 113°–115° C., were obtained.

EXAMPLE 53 cis,trans-11-(4-Methyl-4-oxypiperazin-1-yl)-carboxamidomethylene-5,6-dihydromorphanthridin-6-one×HCl×H₂O 4.0 g (11.5 millimoles) of cis,trans-11-(4-methylpiperazin-1-yl)-carboxamidomethylene-5,6-dihydromorphanthridin-6-one were dissolved in 150 ml of hot ethanol and 4.8 ml of 30% strength hydrogen peroxide were added. The mixture was refluxed for 5 hours and the excess hydrogen peroxide was then destroyed by dropping a small sheet of platinum into the reaction mixture and refluxing the mixture for 2 hours. The reaction mixture was then filtered and concentrated, and the N-oxide obtained was purified by column chromatography (silica gel, mobile phase: a 50/50 methylene chloride/methanol mixture). 3.9 g (89%) of colorless crystals, melting point 180°–182° C., were isolated.

EXAMPLE 54 cis,trans-11-(4-Methylpiperazin-1-yl-carboxamidomethylene-5,6-dihydromorphanthridin-6-one × H₂O A. Preparation of the Wittig phosphonate 17.7 g (177 millimoles) of N-methylpiperazine were added, with thorough stirring, to 20.0 g (177 millimoles) of chloroacetyl chloride in 200 ml of methylene chloride at 0° C., and stirring was then continued for 2 hours at room temperature. Thereafter, the reaction mixture was rendered slightly alkaline with 10% strength sodium hydroxide solution and was stirred for a further 15 minutes at room temperature, the organic phase was separated off and the aqueous phase was extracted twice more with methylene chloride. The combined organic phases were washed with water, dried and concentrated to about 200 ml.

147 g (885 millimoles) of triethyl phosphite were added to this solution of 1-chloroacetyl-4-methyl-piperazine in methylene chloride and the methylene chloride was distilled off under atmospheric pressure, through a packed column. The residue was then heated for 2 hours at 140° C., with continued distillation through the column (resulting in the distillation of ethylene chloride). The triethyl phosphite was then carefully distilled off under reduced pressure from an oilpump, and the residue was purified by column chromatography (silica gel, mobile phase: a 95/5 methylene chloride/methanol mixture). 15 g (31%) of diethyl-4-methylpiperazin-1-yl-phosphonoacetamide were isolated as a yellow oil.

B. Preparation of the end product 7.2 g (32.4 millimoles) of 5,6-dihydro-morphanthridine-6,11-dione were dissolved in 40 ml of dimethylformamide and the solution was stirred under nitrogen. 13.3 g (48.0 millimoles) of diethyl-4-methylpiperazin-1-pl-phosphonoacetamide and 8.4 g (48.0 millimoles) of 30% strength sodium methylate dissolved in 20 ml of dimethylformamide were then slowly dripped in simultaneously (an intensification of the color and rise in temperature indicated the start of the Wittig reaction). The mixture was stirred for a further 12 hours at room temperature, the solvent was then removed under reduced pressure from an oilpump, and the residue was partitioned between water and methylene chloride. The organic phase was concentrated and the crude product was purified by column chromatography (silica gel; a 95/5 methylene chloride/methanol mixture). 4.1 g (35%) of cis,trans-11-(4-methyl-piperazin-1-yl)-carboxamidomethylene-5,6-dihydro-morphanthridin-6-one×H$_2$O, melting point 111°–115° C., were isolated.

Following similar methods, cis,trans-11-dimethylamino-carboxamidomethylene-5,6-dihydro-morphanthridin-6-one (cf. Example 52) and cis,trans-11-piperidin-1-yl-carboxamidomethylene-5,6-dihydromorphanthridin-6-one (cf. Example 11) were obtained.

We claim:

1. A 5,6-dihydro-11-alkylene-morphanthridin-6-one of the formula I

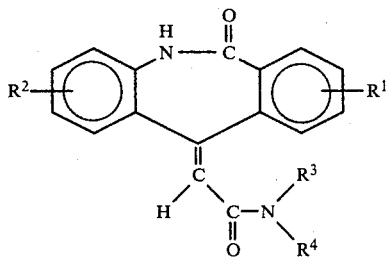

I where R$^1$ and R$^2$ are hydrogen, chlorine or methyl and R$^3$ and R$^4$ together with nitrogen atom by which they are linked form a piperazine ring in which the carbon atoms are unsubstituted or substituted by one or more alkyl radicals of 1 to 3 carbon atoms and the nitrogen atom is substituted by alkyl of 1 to 3 carbon atoms, hydroxylalkyl of 2 or 3 carbon atoms or phenyl which is itself unsubstituted or substituted by fluorine, chlorine, methoxy or methyl, or is in the form of the N-oxide, and/or its physiologically tolerated acid addition salts.

2. A compound of the formula I as set forth in claim 1, in the cis-form.

3. 11-(4-Methylpiperazinyl-1-yl)-carboxamidomethylene-5,6-dihydromorphanthridin-6one.

4. cis-11-(4-Methylpiperazinyl-1-yl)-carboxamidomethylene-5,6-dihydromorphanthridin-6-one.

5. A pharmaceutical composition for treating gastric and duodenal ulcers which comprises: a pharmaceutical auxillary and from 0.001 to 99% by weight of a compound of the formula I of claim 1.

6. A process for treating disorders which are accompanied by pathologically increased gastric secretion which comprises: administering to the patient to be treated a composition as set forth in claim 1 in an amount sufficient to provide a daily dose of a compound of the formula I of from 5 to 100 mg.

* * * * *

UNITED STATES PATENT AND TRADEMARK OFFICE
CERTIFICATE OF CORRECTION

PATENT NO. : 4,399,139
DATED : August 16, 1983
INVENTOR(S) : Gerd STEINER et al.

It is certified that error appears in the above-identified patent and that said Letters Patent is hereby corrected as shown below:

Claim 6, line 4, should read :

"as set forth in claim 5" rather than in "claim 1".

Signed and Sealed this

Eighth Day of November 1983

[SEAL]

Attest:

Attesting Officer

GERALD J. MOSSINGHOFF

*Commissioner of Patents and Trademarks*